United States Patent [19]

Smith

[11] 4,294,759
[45] Oct. 13, 1981

[54] STRUCTURAL ANALOGUES OF 5,6,-DIHYDRO PG₁

[75] Inventor: Herman W. Smith, Kalamazoo, Mich.

[73] Assignee: The Upjohn Company, Kalamazoo, Mich.

[21] Appl. No.: 159,738

[22] Filed: Jun. 16, 1980

Related U.S. Application Data

[63] Continuation-in-part of Ser. No. 94,572, Nov. 15, 1979, abandoned.

[51] Int. Cl.³ .......................................... C07D 209/12
[52] U.S. Cl. ......................... 260/326.27; 260/326.5 B; 542/421; 542/426; 542/429
[58] Field of Search ................... 260/326.27, 326.5 B; 542/421, 426, 429

[56] References Cited

U.S. PATENT DOCUMENTS 4,097,489  6/1978  Bundy ........................... 260/326.27
4,112,224  9/1978  Bundy ................................ 544/137
4,151,176  4/1979  Bundy ........................... 260/326.27
4,161,584  7/1979  Bundy ........................... 260/326.27
4,211,706  7/1980  Bundy ........................... 260/326.27

OTHER PUBLICATIONS

Nicolaou et al., J. Am. Chem. Soc. 101 (1979), pp. 766–768.

Primary Examiner—Arthur P. Demers
Attorney, Agent, or Firm—L. Ruth Hattan; Martin B. Barancik

[57] ABSTRACT

Novel structural analogues of 5,6-dihydro PGI₁ of the formula:

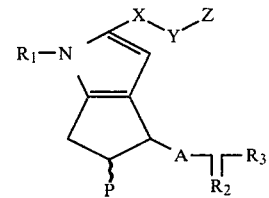

useful as antiallergy agents.

9 Claims, No Drawings

STRUCTURAL ANALOGUES OF 5,6,-DIHYDRO PG₁

CROSS REFERENCE TO RELATED APPLICATION

This application is a continuation-in-part application of co-pending application Ser. No. 94,572, filed Nov. 15, 1979, now abandoned.

SUMMARY OF THE INVENTION

This invention relates to novel structure analogs of 5,6-dihydroprostacyclin ($PGI_1$) and to the use of those compounds as anti-asthma compounds.

Prostacyclin is an endogenously produced compound in mammalian species, being structurally and bisynthetically related to the prostaglandins (PG's). The 5,6-dihydrocompound does not have a double bond between the 5 and 6 positions.

The stereo chemistry including; inter alia, dark lines, broken lines, wavy lines and positioning of the molecule from left to right follow the usual prostacyclin convention. The name of the compounds follows the usual prostacyclin conventions, see Nelson, Med. Chem. 17:911 (1974) and Johnson, R. A., Prostaglandins 15: 737 (1978).

PRIOR ART

Nicolaou, et al., discloses in J. Am. Chem. Soc. 101 (3), 766 (1979) 6,9-pyridazaprostacyclin and its derivatives, the dihydropyridazaprostacyclin and N-oxides. U.S. Pat. No. 4,112,224 discloses bicyclic nitrogen containing compounds which are analogues of the prostaglandins. U.S. Pat. No. 4,097,489 discloses 9-deoxy-9α,6-nitrilo or 6,9α-imino-PGF compounds.

DETAILED DESCRIPTION OF THE INVENTION

In accordance with this invention, there are compounds of Formula I below

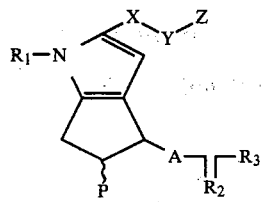

Formula I wherein P is H, OH, or $CH_2OH$;
X is $(CH_2)_n$ wherein n is 2 or 4;
Y is $CH_2$—$CH_2$, —CH=CH— (trans), or $CH_2CF_2$;
Z is
  a. $CO_2R_8$ wherein $R_8$ is hydrogen, alkyl of one to six carbon atoms, inclusive, pharmacologically acceptable metal or amine cation, phenyl, phenyl substituted with one, two or three chloro or alkyl of one to three carbon atoms, inclusive, phenyl substituted in the para position by
    (i) —$NHCOR_{10}$
    (ii) —$COR_{11}$
    (iii) —O—$COR_{12}$
    (iv) —CH=N—$NHCONH_2$
    wherein $R_{10}$ is methyl, phenyl, acetamidophenyl, benzamidophenyl or $NH_2$; $R_{11}$ is methyl, phenyl, $NH_2$ or methoxy; and $R_{12}$ is phenyl or acetamidophenyl;
  b. $CONR_{13}R_{14}$ wherein $R_{13}$ and $R_{14}$ are the same or different and are hydrogen, alkyl of one to six carbon atoms, inclusive, phenyl or benzyl;
  c. $CH_2OR_5$ wherein $R_5$ is hydrogen, alkyl of one to six carbon atoms, inclusive, $COC_6H_5$ or $COCH_3$;
$R_1$ is hydrogen, alkyl of one to four carbon atoms, inclusive, cycloalkyl of three to seven carbon atoms, inclusive;

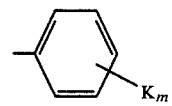

wherein K is alkyl of one to three carbon atoms, inclusive, F, Cl, $CF_3$ or $OCH_3$ and m is 0, 1, 2 or 3, K is further $CO_2R_8$, $R_8$ defined as above; $CH_2OR_5$, $R_5$ defined as above or phenyl;
A is —$CH_2$—$CH_2$, —CH=CH— (cis or trans) or —C≡C—;
$R_2$ is

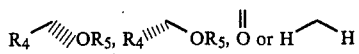

wherein $R_4$ is hydrogen, alkyl of one to three carbon atoms, inclusive, $R_5$ is hydrogen, methyl or $COCH_3$;
$R_3$ is
  a.

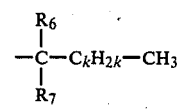

b.

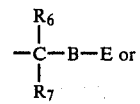

c.

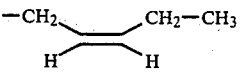

wherein $R_6$ and $R_7$ are hydrogen, fluoro, alkyl of one to four carbon atoms, inclusive, with the proviso that
  (i) when $R_6$ is fluoro, $R_7$ is hydrogen or fluoro or
  (ii) $R_6$ and $R_7$ are not fluoro when B is oxa,
wherein B is a valence bond, oxa, or alkylene of one to six carbon atoms, inclusive, k is 1, 2, 3 or 4;
wherein E is

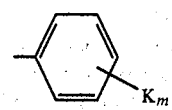

wherein Km is as defined above, the Km of E being the same or different as the Km of $R_1$. These compounds are referred to as Group A. Another group of compounds of the invention are the compounds of Group A wherein
- X is $CH_2$—$CH_2$ or —$(CH_2)_4$;
- Y is —$CH_2$—$CH_2$ or $CH_2CF_2$;
- Z is $CO_2R_8$ wherein $R_8$ is hydrogen, a pharmacologically acceptable metal or amine cation, or methyl;
- $R_1$ is hydrogen, alkyl of one to four carbon atoms, inclusive, cyclohexyl or phenyl;
- A is —CH=CH— (trans), —C≡C—, —$CH_2$—$CH_2$—;
- $R_2$ is

wherein $R_4$ is hydrogen or methyl;
$R_3$ is
a.

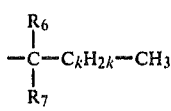

wherein $R_6$ and $R_7$ are the same and are fluoro or methyl and k is 1, 2, 3 or 4, with the proviso that neither $R_6$ nor $R_7$ is fluoro when B is oxa.
b.

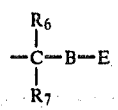

wherein $R_6$ and $R_7$ are the same or different and are hydrogen or methyl,
B is a valence bond, oxa or alkylene of one to six carbon atoms, inclusive;
E is

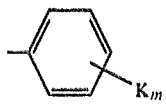

wherein K is fluoro, chloro, trifluoromethyl, or methoxy and m is 0, 1 or 2.
c.

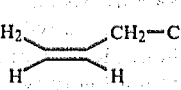

Another group of compounds are those of Group A wherein
- P is ≡OH;
- X is $(CH_2)_2$;
- Y is $(CH_2)_2$ or $CH_2CF_2$;
- Z is $CO_2R_8$ wherein $R_8$ is hydrogen or methyl;
- $R_1$ is hydrogen, methyl or phenyl;
- A is —CH=CH— (trans) or —C≡C—;
- $R_2$ is

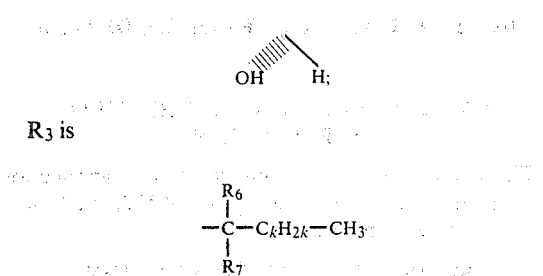

$R_3$ is

wherein $R_6$ and $R_7$ are hydrogen and k is 3.
A further subgroup are those compounds of Group A wherein P is
$\overline{O}H$
- X is $(CH_2)_2$;
- Y is —CH=CH— (trans);
- Z is
  a. $CO_2R_8$ wherein $R_8$ is hydrogen or methyl or
  b. $CONR_{13}R_{14}$ wherein $R_{13}$ is hydrogen and $R_{14}$ is hydrogen, methyl or phenyl;
- $R_1$ is hydrogen or methyl;
- A is —CH=CH— (trans);
- $R_2$ is

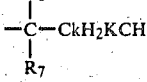

$R_3$ is

where $R_6$ and $R_7$ are hydrogen and k is three.
A further subgroup of compounds are those of Group A wherein P is
$\overline{O}H$
- X is $(CH_2)_2$;
- Y is $(CH_2)_2$;
- Z is $CO_2R_8$ wherein $R_8$ is hydrogen;
- $R_1$ is phenyl;
- A is —CH=CH— (trans);
- $R_2$ is

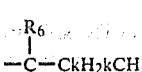

$R_3$ is
a.

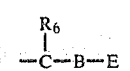

wherein $R_6$ and $R_7$ are methyl and k is 3;
b.

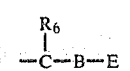

wherein
(i) $R_6$ and $R_7$ are hydrogen, B is $CH_2$ and E is phenyl;
(ii) $R_6$ and $R_7$ are hydrogen, B is oxa and E is phenyl.

As used in this specification and claims, the phrase "alkyl of one to six carbon atoms, inclusive" means methyl, ethyl, propyl, butyl, pentyl, hexyl and isomers thereof, for example isopropyl, tertbutyl, neopentyl and 2,3-dimethylbutyl. Alkyl of a lesser carbon number are interpreted in the same manner.

"Cycloalkyl of three to seven carbon atoms, inclusive" means cyclopropyl, cyclobutyl, cyclopentyl, cyclohexyl and cycloheptyl.

The phrase "pharmacologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, triethanolamine, ethyldiethanolamine, N-butylethanolamine, 2-amino-1-butanol, 2-amino-1-ethyl-1,3-propanediol, 2-amino-2-methyl-1-propanol, tri(hydroxymethyl)aminoethane, N-phenylethanolamine, N-(p-tert-amylphenyl)diethanolamine, galactamine, N-methylglucamine, N-methylglucosamine, ephedrine, phenylephrine, epinephrine, procaine, and the like.

The term "pharmacologically acceptable metal" includes alkali metals such as sodium and potassium, alkaline earth metals such as calcium and magnesium, and other acceptable metals such as aluminum.

Examples of phenyl esters substituted in the para position include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzylphenyl ester, p-amidocarbonylphenyl ester, p-methoxycarbonylphenyl ester, p-benzoyloxyphenyl ester and p-(p-acetamidobenzoyloxy)phenyl ester.

The compounds of this invention are prepared by procedures known in the art. Attention is directed to Chart I wherein the synthetic pathway from known compounds or readily prepared compounds is carried out. It should be noted that the initial starting materials in the synthetic pathway, II or III, are well known prostacyclin analogs or 6-ketoprostaglandin analogs. The process steps from II through VII are known from various prior art references, including Belgium Pat. No. 862,547. It should be noted that the various hydroxy groups in the molecule, for example the 11 position and 15 position of the molecule, should be protected at various steps of the synthesis by a group resistant to the synthetic conditions, for example, tetrahydropyranyl or a silyl ether. The conversion of the 6-keto PGE compound of VII to the pyrrole of VIII is carried out by reacting VII with an appropriate $R_1NH_2$ amine, wherein $R_1$ is defined as in Group A. The P group in the synthesis is any of those in Group A but protected with a group resistant to the reactant conditions, where necessary, for example terminal hydroxy groups, as described above. It is preferable to maintain P as $\overset{\\\\}{\text{OH}}$ or protected $\overset{\\\\}{\text{OH}}$ from II to VII and then at VII converting P to whatever P is desired. Alternatively, the conversion can occur at VIII.

The conversion of the 6-keto PGE compound (VII) to the pyrrole is carried out in a suitable solvent such as a lower alcohol, ether or amide. Examples of lower alcohols include methanol, ethanol, propanol or isopropanol. Examples of ether include diethyl ether, dioxane and tetrahydrofuran. Examples of amides are dimethylformamide and diethylformamide. The temperature at which the reaction takes place is not unduly significant. Temperature of from about 25° to 50° C. can be employed depending upon the reaction velocity desired. Catalytic quantities of an acid such as a mineral acid, for example, hydrochloric or sulfuric acid, an amine hydrochloride for example or an organic sulfonic acid, for example, para toluene sulfonic acid are generally employed.

The hydroxy protective groups can be removed at this stage or prior to the conversion of the 6-keto compound (VII) to the pyrrole of this invention (VIII) by the standard methods for example acidic hydrolysis for removal of tetrahydropyranyl and contact with an anionic fluoride containing compound for removal of the silyl ether.

The following are examples of compounds of the invention. The examples are intended to illustrate and not to limit the invention.

The amine $R_1NH_2$ wherein $R_1$ is hydrogen, alkyl of one to six carbon atoms, inclusive, cycloalkyl of three to seven carbon atoms, inclusive, phenyl or substituted phenyl as defined in Group A are reacted with 6-keto PG compounds of VII having the following structural features:

15-methyl
16-methyl-;
16,16-dimethyl-;
16-fluoro-;
16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-phenoxy-18,19,20-trinor-;
16-methyl-16-phenoxy-18,19,20-trinor-;
16-methyl-13,14-didehydro-;
16,16-dimethyl-13,14-didehydro-;
16-fluoro-13,14-didehydro-;
17-phenyl-18,19,20-trinor-13,14-didehydro-;
17-(m-trifluoromethylphenyl)-18,19,20-trinor-13,14-didehydro-;

17-(m-chlorophenyl)-18,19,20-trinor-13,14-didehydro-;
17-(p-fluorophenyl)-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-phenoxy-18,19,20-trinor-13,14-didehydro-;
16-methyl-16-phenoxy-18,19,20-trinor-13,14-didehydro-;
13,14-dihydro-;
16-methyl-13,14-dihydro-;
16,16-dimethyl-13,14-dihydro-;
16-fluoro-13,14-dihydro-;
16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-phenoxy-18,19,20-trinor-13,14-dihydro-;
16-methyl-16-phenoxy-18,19,20-trinor-13,14-dihydro-;
2,2-difluoro-;
2,2-difluoro-16-methyl-;
2,2-difluoro-16,16-dimethyl-;
2,2-difluoro-16-fluoro-;
2,2-difluoro-16,16-difluoro-;
2,2-difluoro-17-phenyl-18,19,20-trinor-;
2,2-difluoro-17-(m-trifluoromethylphenyl)-18,19,20-trinor-;
2,2-difluoro-17-(m-chlorophenyl)-18,19,20-trinor-;
2,2-difluoro-17-(p-fluorophenyl)-18,19,20-trinor-;
2,2-difluoro-16-methyl-17-phenyl-18,19,20-trinor-;
2,2-difluoro-16,16-dimethyl-17-phenyl-18,19,20-trinor-;
2,2-difluoro-16-fluoro-17-phenyl-18,19,20-trinor-;
2,2-difluoro-16,16-difluoro-17-phenyl-18,19,20-trinor-;
2,2-difluoro-16-phenoxy-17,18,19,20-tetranor-;
2,2-difluoro-16-(m-trifluoromethylphenoxy)-17,18,19,20-tetranor-;
2,2-difluoro-16-(m-chlorophenoxy)-17,18,19,20-tetranor-;
2,2-difluoro-16-phenoxy-18,19,20-trinor-;
2,2-difluoro-16-methyl-16-phenoxy-18,19,20-trinor-;
2,2-difluoro-16-methyl-13,14-didehydro-;
2,2-difluoro-16,16-dimethyl-13,14-didehydro-;
2,2-difluoro-16-fluoro-13,14-didehydro-;
2,2-difluoro-16,16-difluoro-13,14-didehydro-;
2,2-difluoro-17-phenyl-18,19,20-trinor-13,14-didehydro-;
2,2-difluoro-17-(m-trifluoromethylphenyl)-18,19,20-trinor-13,14-didehydro-;
2,2-difluoro-17-(m-chlorophenyl)-18,19,20-trinor-13,14-didehydro-;
2,2-difluoro-17-(p-fluorophenyl)-18,19,20-trinor-13,14-didehydro-;
2,2-difluoro-16-methyl-17-phenyl-18,19,20-trinor-13,14-didehydro-;
2,2-difluoro-16,16-dimethyl-17-phenyl-18,19,20-trinor-13,14-didehydro-;
2,2,16-trifluoro-17-phenyl-18,19,20-trinor-13,14-didehydro-;
2,2,16,16-tetrafluoro-17-phenyl-18,19,20-trinor-13,14-didehydro-;
2,2-difluoro-16-phenoxy-17,18,19,20-tetranor-13,14-didehydro-;
2,2-difluoro-16-(m-trifluoromethylphenoxy)-17,18,19,20-tetranor-13,14-didehydro-;
2,2-difluoro-16-(m-chlorophenoxy)-17,18,19,20-tetranor-13,14-didehydro-;
2,2-difluoro-16-phenoxy-18,19,20-trinor-13,14-didehydro-;
2,2-difluoro-16-methyl-16-phenoxy-18,19,20-trinor-13,14-didehydro-;
2,2-difluoro-13,14-dihydro-;
2,2-difluoro-16-methyl-13,14-dihydro;
2,2-difluoro-16,16-dimethyl-13,14-dihydro-;
2,2,16-trifluoro-13,14-dihydro-;
2,2,16,16-tetrafluoro-13,14-dihydro-;
2,2-difluoro-17-phenyl-18,19,20-trinor-13,14-dihydro-;
2,2-difluoro-17-(m-trifluoromethylphenyl)-18,19,20-trinor-13,14-dihydro-;
2,2-difluoro-17-(m-chlorophenyl)-18,19,20-trinor-13,14-dihydro-;
2,2-difluoro-17-(p-fluorophenyl)-18,19,20-trinor-13,14-dihydro-;
2,2-difluoro-16-methyl-17-phenyl-18,19,20-trinor-13,14-dihydro-;
2,2-difluoro-16,16-dimethyl-17-phenyl-18,19,20-trinor-13,14-dihydro-;
2,2,16-trifluoro-17-phenyl-18,19,20-trinor-13,14-dihydro-;
2,2,16,16-tetrafluoro-17-phenyl-18,19,20-trinor-13,14-dihydro-;
2,2-difluoro-16-phenoxy-17,18,19,20-tetranor-13,14-dihydro-;
2,2-difluoro-16-(m-trifluoromethylphenoxy)-17,18,19,20-tetranor-13,14-dihydro-;
2,2-difluoro-16-(m-chlorophenoxy)-17,18,19,20-tetranor-13,14-dihydro-;
2,2-difluoro-16-(p-fluorophenoxy-17,18,19,20-tetranor-13,14-dihydro-;
2,2-difluoro-16-phenoxy-18,19,20-trinor-13,14-dihydro-;
2,2-difluoro-16-methyl-16-phenoxy-18,19,20-trinor-13,14-dihydro-;
16-methyl-cis-13;
16,16-dimethyl-trans-13-;
16-fluoro-cis-13-;
16,16-difluoro-trans-13-;

17-phenyl-18,19,20-trinor-cis-13-;
17-(m-trifluoromethylphenyl)-18,19,20-trinor-trans-13-;
17-(m-chlorophenyl)-18,19,20-trinor-cis-13-;
17-(p-fluorophenyl)-18,19,20-trinor-trans-13-;
16-methyl-17-phenyl-18,19,20-trinor-cis-13-;
16,16-dimethyl-17-phenyl-18,19,20-trinor-trans-13-;
16-fluoro-17-phenyl-18,19,20-trinor-cis-13-;
16,16-difluoro-17-phenyl-18,19,20-trinor-trans-13-;
16-phenoxy-17,18,19,20-tetranor-cis-13-;
16-(m-trifluoromethylphenoxy)-17,18,19,20-tetranor-trans-13-;
16-(m-chlorophenoxy)-17,18,19,20-tetranor-cis-13-;
16-(p-fluorophenoxy)-17,18,19,20-tetranor-trans-13-;
16-phenoxy-18,19,20-trinor-cis-13-;
16-methyl-16-phenoxy-18,19,20-trinor-trans-13-;
2,2-difluoro-cis-13-;
2,2-difluoro-16-methyl-trans-13-;
2,2-difluoro-16,16-dimethyl-cis-13-;
2,2-difluoro-16-fluoro-trans-13-;
2,2-difluoro-16,16-difluoro-cis-13-;
2,2-difluoro-17-phenyl-18,19,20-trinor-trans-13-;
2,2-difluoro-17-(m-trifluoromethylphenyl)-18,19,20-trinor-cis-13-;
2,2-difluoro-17-(m-chlorophenyl)-18,19,20-trinor-trans-13-;
2,2-difluoro-17-(p-fluorophenyl)-18,19,20-trinor-cis-13-;
2,2-difluoro-16-methyl-17-phenyl-18,19,20-trinor-trans-13-;
2,2-difluoro-16,16-dimethyl-17-phenyl-18,19,20-trinor-cis-13-;
2,2-difluoro-16-fluoro-17-phenyl-18,19,20-trinor-trans-13-;
2,2-difluoro-16,16-difluoro-17-phenyl-18,19,20-trinor-cis-13-;
2,2-difluoro-16-fluoro-18-phenyl-19,20-dinor-trans-13-;
2,2-difluoro-16,16-difluoro-18-phenyl-19,20-dinor-cis-13-;
2,2-difluoro-16-phenoxy-17,18,19,20-tetranor-trans-13-;
2,2-difluoro-16-(m-trifluoromethylphenoxy)-17,18,19,20-tetranor-cis-13-;
2,2-difluoro-16-(m-chlorophenoxy)-17,18,19,20-tetranor-trans-13-;
2,2-difluoro-16-(p-fluorophenoxy)-17,18,19,20-tetranor-cis-13-;
2,2-difluoro-16-phenoxy-18,19,20-trinor-trans-13-;
2,2-difluoro-16-methyl-16-phenoxy-18,19,20-trinor-cis-13-;
2,3-didehydro-;
trans-2,3-dehydro-;
15-keto-2,2-difluoro-;
15-dihydro-;
15-methoxy;
15-methoxy-13,14-dihydro-;
15-acetyl-;
15-methoxy;
15-acetyl-17-phenoxy-18,19,20-trinor-;
15-acetyl-13-trans-;
20 methyl-;
20 nor-;
19,20-dinor-;
15-ethyl-18,19,20-trinor-;
15-methyl-18,19,20-trinor-;
13,14-didehydro;
2-trans-20-nor-;
15-ethyl-15-methoxy, 18,19,20-trinor-;
16-difluoro-ethylenyl-19-phenyl-20-nor-;
18-p-chlorophenyl-20-nor-;
cis-17,18-dehydro-;
2,2-difluoro-cis-17,18-dehydro-;
13,14-dihydro-17,18-dehydro-;
trans-2-cis-17,18-dehydro-;
1a, 1b-dihomo-cis-17,18-dehydro-;
trans-2-3a, 3b-dihomo-trans-13,14-dehydro-16-phenoxy-18,19,20-trinor-;

Following preparation of compound VIII as the acid, Z is COOH, the Z grouping can be changed by conventional chemistry to any of the Z groups defined in Group A. Likewise, if the P group is not as desired, it can also be readily converted into the desired group by standard chemical means.

Following are specific examples of the invention.

EXAMPLE 1

I. 9-Deoxy-6,9-N-phenylimino-$\Delta^{6,8}$-PGI methyl ester 1a. 5ξ-Iodo-9-deoxy-6ε,9α-epoxy-11,15-bis-dimethyl-t-butylsilyl ether A solution of 5ε-iodo-9-deoxy-6ε,9α-epoxy PGF$_1\alpha$ (11.0 g) in DMF (50 ml) is treated with imidazole (8.86 g) and t-butyldimethylchlorosilane (7.85 g) and reacted for two hours. The suspension is diluted with H$_2$O and extracted with ethyl acetate. Drying and evaporation of the extract gave 15 g of pale yellow oil. Purification on silica gel (360 g) with 97:3 hexane:ethyl acetate (260 ml fractions) gives 10.9 g of 1a.

1b. 6-Keto-PGF$_1\alpha$ bis-dimethyl-t-butylsilyl ether methyl ester

A solution of 1a (10.9 g) in toluene (50 ml) is treated with diazabicyclononene (12.5 ml) and reacted for 19 hours. Additional reagent (8.2 ml) is added and the suspension reacted for six hours. The reaction is diluted with ethyl acetate, partitioned with H$_2$O, dried and evaporated to a green oil.

The crude oil is hydrolyzed in acetonitrile (5 ml) with 4% acetic acid in 90% aqueous acetonitrile for 45 minutes, diluted with 0.2 M KHSO$_4$, extracted with ether, and the combined extracts washed with H$_2$O. Drying and evaporation of solvent gives a two-product mixture (8.96 g).

Purification on silica gel (440 g) with 85:15 hexane:ethyl acetate (40 ml fractions) gives 1.65 g of impure hemi-acetal; 7:3 hexane:ethyl acetate elution (fractions 10–43) gives 7.1 g of 1b containing 25–30% of the hemiacetal, Rf 0.40 and 0.77, respectively in 3:1 cyclohexane; ethyl acetate; Rf 0.08 and 0.31, respectively, in 9:1 cyclohexane:ethyl acetate.

1c. 6-Keto-PGF$_{1\alpha}$ 9-acetate-11,15-bis-t-butyldimethylsilyl ether methyl ester A solution of crude 1b (5.1 g) in pyridine (20 ml) is treated with acetic anhydride and reacted for 65 hours. The solution is cooled, diluted with 5% NaCl and extracted with ether. The extract is washed, dried and evaporated to yield crude 1c as a pale yellow oil (5.78 g).

Fractionation on silica gel (425 g) with 9:1 hexane:ethyl acetate (fractions 1–19) and 8.5:1.5 hexane:ethyl acetate (fractions 20–46) gives 1c (3.83 g) in fractions 21–29.

1d. 6-Keto-PGF$_{1\alpha}$ 11,15-bis-t-5-butyldimethylsilyl ether

A solution of 1c (1.43 g) in dimethylformamide (90 ml) is treated with 2.2 N NaOH (10 ml) and the turbid mixture treated with H$_2$O (12 ml). The solution is heated at 80°–87° C. for 1.5 hours, cooled, acidified with 0.2 M KHSO$_4$ and extracted with ethyl acetate. The extract is washed, dried and evaporated to yield 1d (1.01 g) as a pale yellow oil, Rf 0.27 in solvent 2:1 cyclohexane; Organic layer from 9:2:5:10 ethyl acetate:acetic acid:cyclohexane:water. Neat storage at 4° C. produces an impurity (ca. 20%) at Rf 0.34.

The sample is combined with product (2.8 g) from duplicate hydrolysis and purified on CC-4 silica gel (430 g) with 9:1 hexane:ethyl acetate collecting 48 ml fractions for fractions 1–84 and 8.5:1.5 for fractions 85–168 (55 ml fractions). Fractions 130–168 provides 2.58 g (61%) of 1d.

1e. 6-Keto-PGE$_1$, 11,15-bis-t-butyldimethyl silyl ether

A solution of 1d (2.5 g) in acetone (45 ml) at −40° C. was treated with 2.67 M Jones reagent (3.25 ml), brought to −20° C. during eight minutes and reacted at −20° C. for 75 minutes. The suspension is diluted with cold 5% NaCl, extracted with ether and the combined extracts are washed with 5% NaCl. Drying and evaporation of solvent gave 2.0 g of yellow oil. Fractionation on CC-4 silica gel (210 g) with 8.5:1.5 (50 ml fractions) removes polar impurities. Fractions 23–50 gives pure 1e (0.85 g), Rf 0.25 in 2:1 cyclohexane:organic layer from 9:2:5:10 ethyl acetate:acetic acid:cyclohexane:water.

1f. 9-Deoxy-6,9-N-phenylimino-$\Delta^{6,8}$-PGI$_2$ 11,15-bis-t-butyldimethylsilyl ether methyl ester A solution of 1e (0.85 g) in ethanol (2 ml) is treated with 1 M aniline in ethanol (10 ml) and 0.1 M pyridine hydrochloride in methylene chloride (0.08 ml) and reacted for 26 hours. The solution is diluted with ether, washed with 0.2 M KHSO$_4$ and 5NaCl solutions, dried and evaporated to yield crude 1f. Without purification, the prepared acid is esterified with excess ethereal diazomethane to yield crude 1f (0.90 g).

Fractionation on CC-4 silica gel with 95:5 hexane:ethyl acetate (18 ml fractions) gives pure 1f (0.52 g), Rf 0.53, 0.66 in 2:1 cyclohexane: organic layer from 9:2:5:10 ethyl acetate:acetic acid:cyclohexane:water, and (9:1 cyclohexane:ethyl acetate, respectively, in fractions 6–13. Pure acid (0.116 g) is obtained in fractions 29–64 (Rf 0.45 in 2:1 cyclohexane:organic layer from 9:2:5:10 ethyl acetate:acetic acid:cyclohexane:water.

1g. 9-Deoxy-6,9-N-phenylimino-$\Delta^{6,8}$1-PGI$_1$ methyl ester

A solution of 1f (0.51 g) in tetrahydrofuran (THF) is treated with 1.2 M tetrabutylammonium fluoride in THF (5 ml) and reacted for 1.5 hours. The dark solution is diluted with ether, washed with 0.2 M KHSO$_4$ and 5% NaCl solutions, dried and evaporated. The residue (0.42 g) is purified on CC-4 silica gel (60 g), collecting 17 ml fractions. Fractions 95–120 (3:2 hexane:ethyl acetate) provides 78 mg of 1 g, (product compound), m.p. 95.5° C. after ether-hexane crystallization.

IR (mull) 965, 1060, 1495, 1605, 1745, 2975, 3425 cm$^{-1}$.

Ultraviolet (Ethanol) 233 ($\epsilon$ 11,400) nm.

Example 2 9-Deoxy-6,9-N-phenylimino-$\Delta$6,8-PGI$_1$

A solution of 9-deoxy-6,9-N-phenylimino-$\Delta$6,8-PGI$_1$ methyl ester (0.320 g) in methanol (20 ml) and 1 N sodium hydroxide (4 ml) is reacted at 25° C. for 18 hours. The solution is acidified with 1 M citric acid and the precipitate is collected to yield 0.274 g of the product compound. Recrystallization from methylene chloride-hexane gives the product compound, m.p. 140.5°.

Example 3

9-Deoxy-6,9-N-phenylimino-$\Delta$6,8-13,14-dihydro-PGI$_1$ 3a. 9-Deoxy-6,9-N-phenylimino-$\Delta$6,8-13,14-dihydro-PGI$_1$ methyl ester di-tetrahydropyranyl ether A solution of 13,14-dihydro-6-keto-PGE$_1$ ditetrahydropyranyl ether (0.31 g) in ethanol (0.5 ml) is treated with 1 M aniline in ethanol (4.0 ml) and 0.1 M pyridine hydrochloride in CH$_2$Cl$_2$ (0.05 ml). The solution is reacted at 25° C. for 7 hours, diluted with ether and washed with 0.2 M KHSO$_4$ and 5% NaCl solutions. Drying and evaporation of solvent gives crude 3a (0.35 g). The sample is combined with 0.36 g of crude 3a from a duplicate preparation and fractionated on CC-4 silica gel (60 g) with 8.5:1.5 hexane:ethyl acetate (55 ml fractions). Fractions 10–16 gives 0.326 g of 3a, RF 0.58 in 1.5:1 organic layer from 9:2:5:10 ethyl acetate:acetic acid:cyclohexane:water to cyclohexane.

3b. 9-Deoxy-6,9-N-phenylimino-$\Delta$6,8-13,14-dihydro-PGI$_1$

A solution of 3a (0.326 g) in acetic acid (8 ml) and water (3 ml) is reacted at 40° C. for 50 minutes. The purple solution is diluted with ether. Immediate color discharge is observed. The solution is washed with 5% NaCl, dried and evaporated. The residue deposits 68 mg of product compound (Rf 0.40 in 3:1 organic layer 9:2:5:10 ethylacetate:acetic acid:cyclohexane:water to cyclohexane from ether hexane.

IR (mull) 900, 1045, 1057, 1115, 1178, 1200, 1255, 1495, 1580, 1695, 2600 (sh), 3200 cm$^{-1}$ Example 4

9-Deoxy-6,9-N-phenylimino-$\Delta$6,8-13,14-dihydro-PGI$_1$ methyl ester

A solution of 9-deoxy-6,9-N-phenylimino-$\Delta$6,8-13,14-dihydro-PGI$_{12}$ (68 mg) is reacted with excess ethereal diazomethane. The solution is washed with 0.2 M KHSO$_4$, 5% NaCl and 5% NaHCO$_3$ solutions. Drying and evaporation of solvent gives a crystalline yellow residue. Purification on silica gel (12 g) with 3:2 hexane:ethyl acetate (15 ml fractions) gives the product compound which deposits (25 mg), Rf 0.51 in 2:1 cyclohexane:ethyl acetate, from ether-hexane.

The administration of the compounds of the present invention to humans and animals provide a method for the prophylactic or therapeutic treatment of allergy of a reagin or non-reagin mediated nature. Asthma is preferably treated but any allergy wherein slow reacting substance of anaphylaxis (SRSA) is thought to be involved as a pharmacological mediator of anaphylaxis can be treated. For example, the compounds can be used for treatment of such conditions as allergic rhinitis, food allergy and urticaria as well as asthma.

An effective but essentially non-toxic quantity of the compound is employed in treatment. The dosage of the compound used in treatment depends on the route of administration and the potency of the particular compound. A dosage schedule for humans of from about 0.1 to about 20 mg. of compound in a single dose, administered parenterally or by inhalation in the compositions of this invention are effective for preventing or diminishing the severity of allergy attacks. More specifically, the single dose is from about 0.5 to about 10 mg. of compound. The oral dose is from about 2 to about 200 mg. in a single dose. More specifically, the single dose is from about 5 to about 100 mg. of compound. The dosage is repeated up to four times daily.

The compounds are compounded into compositions for administration. The compositions of the present invention are presented for administration to humans and animals in unit dosage forms, such as tablets, capsules, pills, powders, granules, sterile parenteral solutions or suspensions, eye drops, oral solutions or suspensions, and oil in water and water in oil emulsions containing suitable quantities of the compound of Formula I.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide or an equivalent gas before suspending in the sterile vehicle. Advantageously, a surfactant or wetting agent is included in the composition to facilitate uniform distribution of the compound.

Compositions for inhalation are of three basic types:
(1) a powder mixture preferably micropulverized with particle size, preferably from about 2 to about 5 microns;
(2) an aqueous solution to be sprayed with a nebulizer;
(3) an aerosol with volatile propellant in a pressurized container.

The powders are quite simply prepared by mixing a compound of Formula I with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl or propyl chlorides. Further suitable liquefied propellants are the fluorinated and fluorochlorinated lower alkanes such as are sold under the trademarks "Freon" and "Genetron." Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in coated tablets, powder packets, wafers, granulates, cachets, teaspoonfuls, tablespoonsfuls, dropperfuls, ampoules, vials, aerosols with metered discharges, segregated multiples of any of the foregoing, and other forms as herein described.

I claim:

CHART I

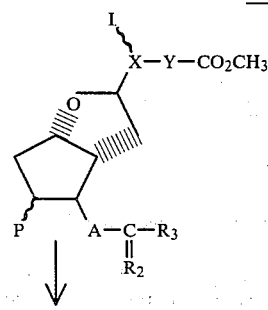

CHART I -continued

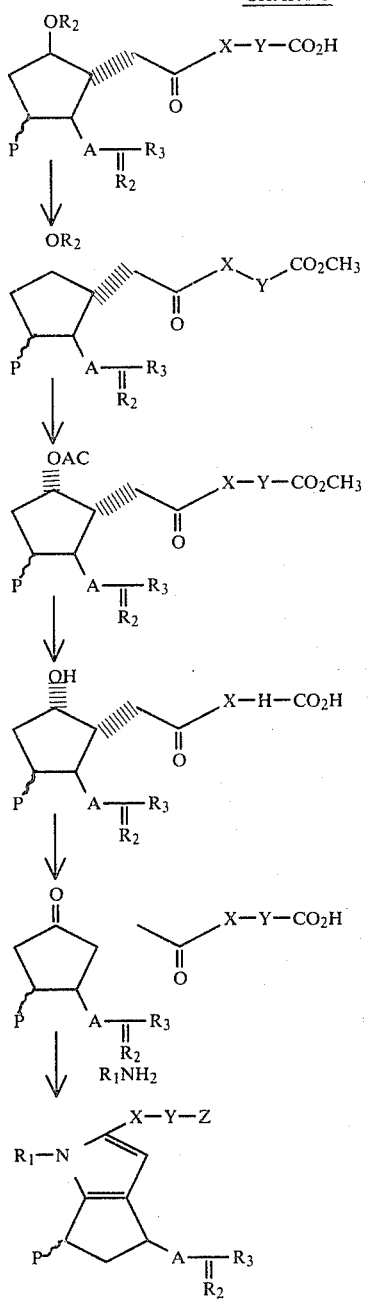

1. A compound of the formula

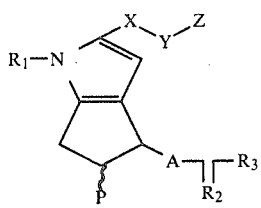

Formula I wherein P is H, OH, or CH₂OH;
X is $(CH_2)_n$ wherein n is 2 or 4;
Y is $CH_2-CH_2$, $-CH=CH-$ (trans), or $CH_2CF_2$;
Z is
  a. $CO_2R_8$ wherein $R_8$ is hydrogen, alkyl of one to six carbon atoms, inclusive, phenyl or a pharmacologically acceptable metal or amine cation, phenyl, phenyl substituted with one, two or three chloro or alkyl of one to three carbon atoms, inclusive, phenyl substituted in the para position by
    (i) $NHCOR_{10}$
    (ii) $COR_{11}$
    (iii) $OCOR_{12}$
    (iv) $CH=NNHCONH_2$
  wherein $R_{10}$ is methyl, phenyl, acetamidophenyl, benzamidophenyl or $NH_2$, $R_{11}$ is methyl, phenyl, $NH_2$ or methoxy; and $R_{12}$ is phenyl or acetamidophenyl;
  b. $CONR_{13}R_{14}$ wherein $R_{13}$ and $R_{14}$ are the same or different and are hydrogen, alkyl of one to six carbon atoms, inclusive, phenyl or benzyl, or
  c. $CH_2OR_5$ wherein $R_5$ is hydrogen, alkyl or one to six carbon atoms, inclusive, $COC_6H_5$ or $COCH_3$;

$R_1$ is hydrogen, alkyl of one to four carbon atoms, inclusive, cycloalkyl three to seven carbon atoms, inclusive,

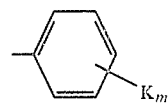

wherein K is alkyl of one to three carbon atoms, inclusive, F, Cl, $CF_3$ or $OCH_3$ and m is 0, 1, 2 or 3, K is further $CO_2R_8$, $R_8$ defined as above, $CH_2OR_5$, $R_5$ defined as above or phenyl;

A is $-CH_2-CH_2$, $-CH=CH-$ (cis or trans) or $-C\equiv C-$;

$R_2$ is

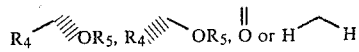

wherein $R_4$ is hydrogen, alkyl of one to three carbon atoms, inclusive, $R_5$ is hydrogen, methyl or $COCH_3$;

$R_3$ is
a.

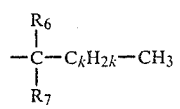

b.

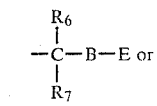

c.

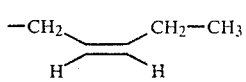

wherein $R_6$ and $R_7$ are hydrogen, fluoro, alkyl of one to four carbon atoms, inclusive, with the proviso that
  (i) when $R_6$ is fluoro, $R_7$ is hydrogen or fluoro or (ii) $R_6$ and $R_7$ are not fluoro when B is oxa, wherein B is a valence bond, oxa, or alkylene of one to six carbon atoms, inclusive, k is 1, 2, 3 or 4;
wherein E is

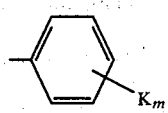

wherein Km is as defined above, the Km of E being the same or different as the Km of $R_1$.

2. A compound in accordance with claim 1 wherein:
X is $CH_2$—$CH_2$ or —$(CH_2)_4$;
Y is —$CH_2$—$CH_2$ or $CH_2CF_2$;
Z is $CO_2R_8$ wherein $R_8$ is hydrogen, pharmacologically acceptable metal or amine cation, or methyl;
$R_1$ is hydrogen, alkyl of one to four carbon atoms, inclusive, cyclohexyl or phenyl;
A is —CH=CH— (trans), —C≡C—, or —CH$_2$—CH$_2$—;
$R_2$ is

wherein $R_4$ is hydrogen or methyl;
$R_3$ is
a.

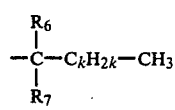

wherein $R_6$ and $R_7$ are the same and are fluoro or methyl and k is 1, 2, 3 or 4, with the proviso that neither $R_6$ nor $R_7$ is fluoro when B is oxa,
b.

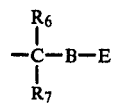

wherein $R_6$ and $R_7$ are the same or different and are hydrogen or methyl,
B is a valence bond, oxa or alkylene of one to six carbon atoms, inclusive;
E is

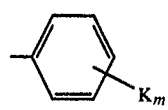

wherein K is fluoro, chloro, trifluoromethyl, or methoxy and m is 0, 1 or 2;
c.

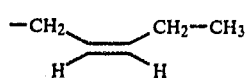

3. A compound in accordance with claim 1 wherein
P is $\overline{\overline{OH}}$
X is $(CH_2)_2$;
Y is $(CH_2)_2$ or $CH_2CF_2$;
Z is $CO_2R_8$ wherein $R_8$ is hydrogen or methyl;
$R_1$ is hydrogen, methyl or phenyl;
A is —CH=CH— (trans) or —C≡C—;
$R_2$ is

$R_3$ is

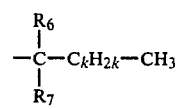

wherein $R_6$ and $R_7$ are hydrogen and k is three.

4. A compound in accordance with claim 1 wherein
P is $\overline{\overline{OH}}$
X is $(CH_2)_2$;
Y is —CH=CH— (trans);
Z is
a. $CO_2R_8$ wherein $R_8$ is a hydrogen or methyl or
b. $CONR_{13}R_{14}$ wherein $R_{13}$ is hydrogen and $R_{14}$ is hydrogen, methyl or phenyl;
$R_1$ is hydrogen or methyl;
A is —CH=CH— (trans);
$R_2$ is

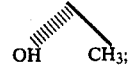

$R_3$ is

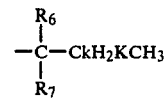

wherein $R_6$ and $R_7$ are hydrogen and k is 3.

5. A compound in accordance with claim 1 wherein
P is $\overline{\overline{OH}}$
X is $(CH_2)_2$;
Y is $(CH_2)_2$;
Z is $CO_2R_8$ wherein $R_8$ is hydrogen;
$R_1$ is phenyl;
A is —CH=CH— (trans);
$R_2$ is

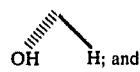

$R_3$ is
a.

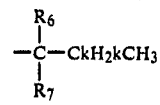

wherein $R_6$ and $R_7$ are methyl and k is 3, or
b.

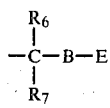

wherein (1) $R_6$ and $R_7$ are hydrogen, B is $CH_2$ and E is phenyl, or (2) $R_6$ and $R_7$ are hydrogen, B is oxa and E is phenyl.

6. 9-Deoxy-6,9-N-phenylimino-$\Delta$6,8-$PGI_1$ methyl ester according to claim 1.

7. 9-Deoxy-6,9-N-phenylimino-$\Delta$6,8-$PGI_1$ according to claim 1.

8. 9-Deoxy-6,9-N-phenylimino-$\Delta$6,8-13,14-dihydro-$PGI_1$ methyl ester according to claim 1.

9. 9-Deoxy-6,9-N-phenylimino-$\Delta$6,8-13,14-dihydro-$PGI_1$ according to claim 1.

* * * * *